(12) United States Patent
Kiya et al.

(10) Patent No.: US 6,313,351 B1
(45) Date of Patent: Nov. 6, 2001

(54) PROCESS FOR PRODUCING ALICYCLIC MONOKETONES AND PROCESS FOR PRODUCING ALICYCLIC DIKETONES

(75) Inventors: Norimoto Kiya; Shinsaku Kawasaki; Kenji Ekawa; Kenji Sugiyama; Toyokazu Kitaura, all of Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/389,079

(22) Filed: Sep. 2, 1999

(30) Foreign Application Priority Data

Jul. 15, 1999 (JP) .................................................. 11-201959

(51) Int. Cl.$^7$ .................................................. C07C 45/62
(52) U.S. Cl. ........................ 568/309; 568/322; 568/324; 568/329; 568/338; 568/362
(58) Field of Search .................................. 568/309, 322, 568/329, 338, 362, 324

(56) References Cited

FOREIGN PATENT DOCUMENTS

| 4059742 | 2/1992 | (JP) . |
| 08134009 | 5/1996 | (JP) . |

*Primary Examiner*—Sreeni Padmanabhan
(74) *Attorney, Agent, or Firm*—Birch, Stewart, Kolasch & Birch, LLP

(57) ABSTRACT

The process for producing alicyclic monoketones (hydroxyphenylcyclohexanone derivatives) according to the present invention comprises hydrogenating substituted bisphenols such as bisphenol A in a solvent in the presence of a palladium/alkali metal catalyst in which palladium and an alkali metal are both supported on a carrier to obtain alicyclic monoketones such as 2-(4-oxocyclohexyl)-2-(4-hydroxyphenyl)propane. The process for producing alicyclic diketones according to the present invention comprises hydrogenating substituted bisphenols such as bisphenol A in a solvent in the presence of a palladium/alkali metal catalyst in which palladium and an alkali metal are both supported on a carrier to obtain alicyclic diketones such as 2,2-bis(4-oxocyclohexyl)propane and 4,4'-bicyclohexanone. The other process for producing alicyclic monoketones according to the present invention comprises hydrogenating biphenols such as bis(4-hydroxyphenyl) in an organic solvent in the presence of a palladium catalyst in which 10 to 30% by weight of palladium is supported on a carrier to obtain alicyclic monoketones such as 4(4'-hydroxyphenyl) cyclohexanone. According to the present invention, alicyclic monoketones or alicyclic diketones can be obtained with high selectivity and in high yields through simple steps, because the process includes only one reaction step to hydrogenate substituted bisphenols under relatively mild conditions.

21 Claims, No Drawings

PROCESS FOR PRODUCING ALICYCLIC MONOKETONES AND PROCESS FOR PRODUCING ALICYCLIC DIKETONES

FIELD OF THE INVENTION

The present invention relates to a process for producing alicyclic monoketones (hydroxyphenylcyclohexanone derivatives) and a process for producing alicyclic diketones. More particularly, the invention relates to a process for producing alicyclic monoketones in which alicyclic monoketones can be obtained in high yields by hydrogenating (reducing) substituted bisphenols in an organic solvent and to a process for producing diketones in which alicyclic diketones can be obtained in high yields by hydrogenating (reducing) substituted bisphenols in an organic solvent.

BACKGROUND OF THE INVENTION

Alicyclic diketones such as 2,2-bis(4-oxocyclohexyl) propane are useful compounds as intermediates of materials of medicines, materials of industrial chemicals, materials of polymers, polymerization initiators, heat resistance improvers, antioxidants and the like.

As a process for producing alicyclic diketones, a process comprising oxidizing alicyclic diol to produce alicyclic diketones has be en known for a long time. For example, Japanese Patent Laid-Open Publication No. 59742/1992 describes a process for producing 2,2-bis(4-oxocyclohexyl) propane, which comprises oxidizing 2,2-bis(4-hydroxycyclohexyl)propane by hypochlorous acid and the like in the presence of a solvent.

The process described in Japanese Patent Laid-Open Publication No. 59742/1992, however, has a problem of using expensive alicyclic diol. If 2,2-bis(4-hydroxyphenyl) propane that is relatively inexpensive is used as a starting material, reactions of two steps, namely, hydrogenation reaction of 2,2-bis(4-hydroxyphenyl)propane and oxidation reaction of 2,2-bis(4-hydroxycyclohexyl)propane obtained by the hydrogenation reaction, must be conducted to produce 2,2-bis(4-oxocyclohexyl)propane, so that the process becomes complicated.

Similarly to the alicyclic diketones, alicyclic monoketones (hydroxyphenylcyclohexanone derivatives) such as 4-(4'-hydroxyphenyl)cyclohexanone and 2-(4-oxocyclohexyl)-2-(4-hydroxyphenyl)propane are also useful as intermediates of materials of medicines, materials of industrial chemicals, materials of polymers, polymerization initiators, heat resistance improvers, antioxidants, liquid crystal compounds for display and the like. However, the aforesaid alicyclic diketones such as 2,2-bis(4-oxocyclohexyl)propane are commonly used as the intermediates, and any literature on the technique to produce alicyclic monoketones was not found as far as the present inventor investigated.

Accordingly, there has been desired development of a process for producing alicyclic diketones by which alicyclic diketones such as 2,2-bis(4-oxocyclohexyl)propane can be obtained in high yields through simple steps using inexpensive materials.

There has been also desired development of a process for producing alicyclic monoketones by which alicyclic monoketones such as 4-(4'-hydroxyphenyl)cyclohexanone and 2-(4-oxocyclohexyl)-2-(4-hydroxyphenyl)propane can be obtained in high yields through simple steps using inexpensive materials.

In connection with the above, Japanese Patent Laid-Open Publication No. 134009/1996 describes a process for producing alicyclic diketones such as 2-(4-oxocyclohexyl)-2-(4-hydroxycyclohexyl)propane, which comprises hydrogenating bisphenols such as bisphenol A in a liquid phase in the presence of a palladium type hydrogenation catalyst and an alkali metal compound with heating under pressure.

OBJECT OF THE INVENTION

It is an object of the present invention to provide a process for producing alicyclic monoketones (hydroxyphenylcyclohexanone derivatives) by which alicyclic monoketones can be obtained with high selectivity and in high yields through simple steps using inexpensive materials. It is another object of the invention to provide a process for producing alicyclic diketones by which alicyclic diketones can be obtained with high selectivity and in high yields through simple steps using inexpensive materials.

SUMMARY OF THE INVENTION

The process for producing alicyclic monoketones (hydroxyphenylcyclohexanone derivatives) according to the present invention comprises hydrogenating substituted bisphenols represented by the following formula (I) in a solvent in the presence of a palladium/alkali metal catalyst in which palladium and an alkali metal are both supported on a carrier, to obtain alicyclic monoketones represented by the following formula (II);

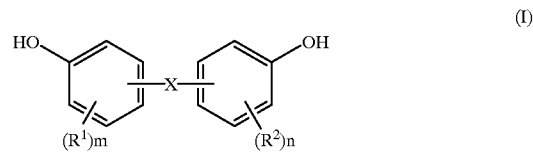

wherein X is a single bond, —$CH_2$—, —$C(CH_3)_2$—, —O— or —$SO_2$—; $R^1$ and $R^2$ are each independently a hydrogen atom or an alkyl group of 1 to 6 carbon atoms; and m and n are each an integer of 0 to 2 and are the same or different;

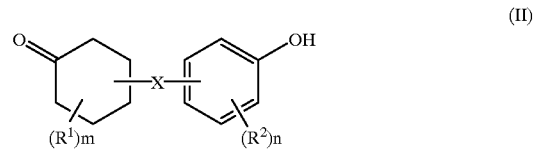

wherein X, $R^1$, $R^2$, m and n have the same meanings as those of X, $R^1$, $R^2$, m and n in the formula (I).

The process for producing alicyclic diketones according to the present invention comprises hydrogenating substituted bisphenols represented by the above formula (I) in a solvent in the presence of a palladium/alkali metal catalyst in which palladium and an alkali metal are both supported on a carrier, to obtain alicyclic diketones represented by the following formula (III):

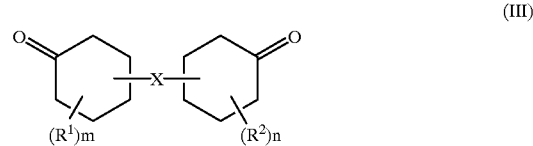

wherein X, $R^1$, $R^2$, m and n have the same meanings as those of X, $R^1$, $R^2$, m and n in the formula (I).

The palladium/alkali metal catalyst in which palladium and an alkali metal are both supported on a carrier is preferably one in which 1 to 10% by weight of palladium and 0.5 to 5% by weight of an alkali metal are both supported on a carrier.

The solvent is preferably a saturated alcohol of 3 or more carbon atoms, particularly preferably a monohydric saturated aliphatic alcohol of 3 to 12 carbon atoms.

The other process for producing alicyclic monoketones according to the present invention comprises hydrogenating substituted biphenols represented by the following formula (I-1) in an organic solvent in the presence of a palladium catalyst in which 10 to 30% by weight of palladium is supported on a carrier, to obtain alicyclic monoketones represented by the following formula (II-1);

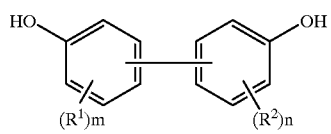

(I-1)

wherein $R^1$ and $R^2$ are each independently a hydrogen atom or an alkyl group of 1 to 6 carbon atoms; and m and n are each an integer of 0 to 2 and are the same or different;

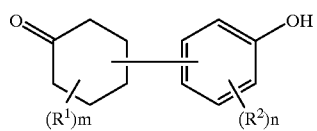

(II-1)

wherein $R^1$, $R^2$, m and n have the same meanings as those of $R^1$, $R^2$, m and n in the formula (I-1).

The organic solvent is preferably a monohydric saturated aliphatic alcohol of 3 to 12 carbon atoms.

In order to obtain alicyclic monoketones represented by the above formula (II) wherein X is a single bond, namely, alicyclic monoketones represented by the above formula (II-1), the latter process for producing alicyclic monoketones according to the invention is preferable because high-purity alicyclic monoketones can be obtained with high selectivity and in high yields.

DETAILED DESCRIPTION OF THE INVENTION

The process for producing alicyclic monoketones (hydroxyphenylcyclohexanone derivatives) and the process for producing alicyclic diketones according to the invention are described in detail hereinafter.

In the process for producing alicyclic monoketones or the process for producing alicyclic diketones according to the invention, hydrogenation of specific substituted biphenols is carried out in a solvent in the presence of a palladium/alkali metal catalyst in which palladium and an alkali metal are both supported on a carrier, to obtain the desired alicyclic monoketones or alicyclic diketones.

In the other process for producing alicyclic monoketones according to the invention, specific substituted biphenols are selectively hydrogenated with hydrogen in an organic solvent, particularly preferably a monohydric alcohol solvent of 3 or more carbon atoms, in the presence of a palladium catalyst in which palladium is supported on a carrier in a high concentration, to obtain the desired alicyclic monoketones.

Substituted Bisphenols

The substituted bisphenols used as starting materials in the process for producing alicyclic monoketones and the process for producing alicyclic diketones according to the invention are represented by the following formula (I). The substituted biphenols used as starting materials in the other process for producing alicyclic monoketones according to the invention are substituted biphenols represented by the following formula (I-1), which are substituted bisphenols represented by the following formula (I) wherein X is a single bond.

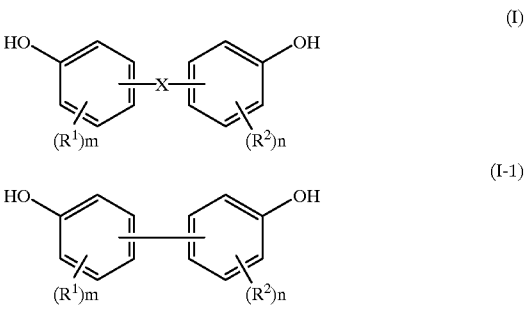

(I)

(I-1)

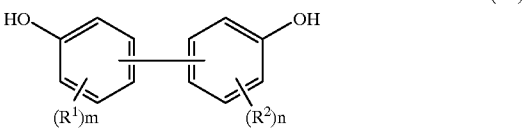

In the formula (I), X is a single bond, —$CH_2$—, —$C(CH_3)_2$—, —O— or —$SO_2$—; $R^1$ and $R^2$ are each independently a hydrogen atom or an alkyl group of 1 to 6 carbon atoms; and m and n are each an integer of 0 to 2 and are the same or different.

In the formula (I-1), $R^1$, $R^2$, m and n have the same meanings as those of $R^1$, $R^2$, m and n in the formula (I).

Examples of the alkyl groups of 1 to 6 carbon atoms indicated by $R^1$ and $R^2$ include methyl, ethyl, n-propyl, isopropyl, n-butyl, isobutyl, s-butyl, t-butyl, pentyl, isopentyl, neopentyl, n-hexyl, 1,3-dimethylbutyl, 2,3-dimethylbutyl and isohexyl groups.

Examples of the substituted bisphenols represented by the formula (I) include:

substituted biphenols wherein X is a single bond, such as bis(4-hydroxyphenyl), bis(2-hydroxyphenyl) and bis(2-methyl-4-hydroxyphenyl);

substituted bisphenols wherein X is a methylene group (—$CH_2$—), such as bis(4-hydroxyphenyl)methane, bis(2-hydroxyphenyl)methane, bis(2-ethyl-4-hydroxyphenyl) methane and (2-hydroxyphenyl)-(4-hydroxyphenyl) methane;

substituted bisphenols wherein X is an isopropylidene group (—$C(CH_3)_2$—), such as 2,2-bis(4-hydroxyphenyl) propane (i.e., bisphenol A), 2,2-bis(2-hydroxyphenyl) propane, 2,2-bis(2-methyl-4-hydroxyphenyl)propane, 2,2-bis(3-methyl-4-hydroxyphenyl)propane and 2-(2-hydroxyphenyl)-2-(4-hydroxyphenyl)propane;

substituted bisphenols wherein X is an oxygen atom, such as bis(4-hydroxyphenyl)ether and bis(2-hydroxyphenyl) ether; and substituted bisphenols wherein X is a sulfonyl group (—$SO_2$—), such as bis(4-hydroxyphenyl)sulfone (i.e., bisphenol S) and bis(2-methyl-4-hydroxyphenyl)sulfone.

Examples of the biphenols represented by the formula (I-1) include the substituted biphenols wherein X is a single bond, which are selected from among the above examples of the substituted bisphenols.

Catalyst

The catalyst for use in the process for producing alicyclic monoketones and the process for producing alicyclic diketones according to the invention is a palladium/alkali metal catalyst in which palladium as a metallic active catalyst component and an alkali metal as a co-catalyst component are both supported on a carrier. This catalyst is referred to as a "palladium/alkali metal catalyst (1)" hereinafter.

The catalyst for use in the other process for producing alicyclic monoketones according to the invention is a palladium catalyst in which palladium as a metallic active catalyst component is supported on a carrier in a high concentration. This catalyst is referred to as a "palladium catalyst (2)" hereinafter.

Palladium/alkali Metal Catalyst (1)

Examples of the carriers for the palladium/alkali metal catalyst (1) include carbon, alumina, silica-alumina, zirconium oxide, titanium oxide and active terra abla. Particularly preferable are carbon and alumina. Examples of the palladium components include metallic palladium, palladium oxide and palladium hydroxide.

The amount of the palladium component supported on the carrier in the palladium/alkali metal catalyst (1) is in the range of 1 to 10% by weight, preferably 3 to 8% by weight, in terms of metallic palladium.

Examples of the alkali metal components include alkali metal hydroxides, such as sodium hydroxide and potassium hydroxide; and alkali metal carbonates, such as anhydrous sodium carbonate (soda ash) and anhydrous potassium carbonate. Of these, sodium hydroxide and anhydrous sodium carbonate are preferable.

In the palladium/alkali metal catalyst (1) for use in the invention, the content of an alkali metal derived from the alkali metal salt is in the range of 0.5 to 5% by weight, preferably 0.5 to 3% by weight, particularly preferably 1.0 to 1.5% by weight. When the palladium/alkali metal catalyst (1) containing the alkali metal in this amount is used in the later-described proportion, the conversion of the substituted bisphenols as the starting materials becomes high, and the selectivity of the desired product (alicyclic monoketones or alicyclic diketones) also becomes high, so that the desired product can be obtained in a high yield.

The conversion, selectivity and yield can be calculated from the following formulas.

Conversion $(\%)=(B/A)\times 100$

Selectivity of alicyclic monoketones or diketones $(\%)=(C/B)\times 100$

Yield of alicyclic monoketones or diketones $(\%)=(C/A)\times 100$

In the above formulas, A is an amount (mol) of the charged substituted bisphenols, B is an amount (mol) of the reacted substituted bisphenols, and C is an amount (mol) of the produced alicyclic monoketones or diketones.

The palladium/alkali metal catalyst (1) generally used is a water-containing catalyst having a water content of about 50%. The shape of the palladium/alkali metal catalyst (1) is not specifically limited, and any shape such as powder or tablet can be appropriately selected according to the type of the reaction.

In the present invention, one or more of the palladium/alkali metal catalysts (1) can be used as a hydrogenation catalyst.

The palladium/alkali metal catalyst (1) for use in the invention can be prepared by allowing the carrier such as carbon to support metallic palladium or the like as a metallic active catalyst component and the alkali metal salt as a co-catalyst component, then drying and calcining at a temperature of 400 to 600° C.

The palladium/alkali metal catalyst (1) is used in an amount of 0.5 to 10 parts by weight, preferably 0.5 to 5 parts by weight, more preferably 1.0 to 3.0 parts by weight, based on 100 parts by weight of the substituted bisphenols as the starting materials.

In the present invention, the desired product can be obtained in an industrially sufficiently high yield even if no co-catalyst is used, but a co-catalyst may be used in combination with the palladium/alkali metal catalyst (1).

Examples of the co-catalysts include hydroxides and carbonates of alkali metals such as sodium and potassium. Of these, an alkali metal carbonate such as sodium carbonate is preferably employed.

The co-catalyst is used in an amount of 0.1 to 1 part by weight, preferably 0.1 to 0.5 part by weight, more preferably 0.1 to 0.2 part by weight, based on 100 parts by weight of the substituted bisphenols as the starting materials.

Palladium Catalyst (2)

Examples of the carriers for the palladium catalyst (2) include the same substances as previously described for the palladium/alkali metal catalyst (1), such as carbon, alumina, silica-alumina, zirconium oxide, titanium oxide and active terra abla. In particular, carbon and alumina are preferable. Examples of the palladium components include the same substances as previously described for the palladium/alkali metal catalyst (1), such as metallic palladium, palladium oxide and palladium hydroxide.

In the palladium catalyst (2) for use in the invention, the amount of the palladium component supported on the carrier is in the range of 10 to 30% by weight, preferably 12 to 29% by weight, more preferably 15 to 28% by weight, in terms of metallic palladium.

When the palladium catalyst (2) in which the palladium component is supported in a high concentration is used in an amount of 0.1 to 5 parts by weight based on 100 parts by weight of the substituted biphenols as the starting materials, the conversion of the substituted biphenols as the starting materials becomes high, and the selectivity of the desired product (hydroxyphenylcyclohexanone derivatives) also becomes high, so that the desired product of high purity can be obtained in a high yield.

The palladium catalyst (2) generally used is a water-containing catalyst having a water content of about 50%. The shape of the palladium catalyst (2) is not specifically limited, and any shape such as powder or tablet can be appropriately selected according to the type of the reaction.

In the present invention, one or more of the palladium catalysts (2) can be used as a hydrogenation catalyst.

The palladium catalyst (2) is used in an amount of 0.1 to 5 parts by weight, preferably 0.1 to 3 parts by weight, more preferably 0.2 to 2 parts by weight, based on 100 parts by weight of the substituted biphenols as the starting materials.

In the process for producing alicyclic monoketones using the palladium catalyst (2) according to the invention, any co-catalyst (e.g., alkali metal compound) serving as a reaction accelerator or the like is not used in the hydrogenation reaction of the substituted biphenols. If a co-catalyst such as an alkali metal compound is used in the hydrogenation of the substituted biphenols in this process of the invention, the selectivity and the yield of the hydroxyphenylcyclohexanone derivatives (monoketones) are lowered.

The conversion, selectivity and yield are calculated in the same manner as previously described with respect to the palladium/alkali metal catalyst (1).

Solvent

In the process for producing alicyclic monoketones using the palladium/alkali metal catalyst (1) or the palladium catalyst (2) according to the invention and in the process for producing alicyclic diketones using the palladium/alkali metal catalyst (1) according to the invention, hydrogenation of the substituted bisphenols is carried out in an organic solvent. When a monohydric saturated alcohol of 3 or more carbon atoms, particularly a monohydric saturated aliphatic alcohol of 3 to 12 carbon atoms, is used as the organic solvent in the invention, the selectivity of the reaction is improved and the starting materials and the reaction products are liable to be dissolved in the solvent.

Examples of the monohydric saturated aliphatic alcohols of 3 to 12 carbon atoms include n-propyl alcohol, isopropyl alcohol, n-butyl alcohol, isobutyl alcohol, sec-butyl alcohol, tert-butyl alcohol, n-amyl alcohol, isoamyl alcohol, n-hexyl alcohol, n-heptyl alcohol, n-octyl alcohol, capryl alcohol (i.e., sec-octyl alcohol), n-nonyl alcohol, n-decyl alcohol, n-undecyl alcohol and lauryl alcohol (i.e., n-dodecyl alcohol). Of these, preferable are sec-butyl alcohol, isopropyl alcohol and capryl alcohol. These solvents can be used singly or in combination.

The solvent is used in an amount of usually 100 to 500 parts by weight, preferably 100 to 300 parts by weight, more preferably 100 to 150 parts by weight, based on 100 parts by weight of the substituted bisphenols, though the amount varies depending on the types of the substituted bisphenols and the solvent. When the saturated alcohol of 3 or more carbon atoms, particularly a monohydric saturated aliphatic alcohol of 3 to 12 carbon atoms, is used in the above amount, the conversion of the substituted bisphenols as the starting materials becomes high, and the selectivity of the desired product (alicyclic monoketones or alicyclic diketones) also becomes high, so that the desired product can be obtained in a high yield.

Hydrogenation of Substituted Bisphenols

Hydrogenation of Substituted Bisphenols by Palladium/alkali Metal Catalyst (1)

Hydrogenation of the substituted bisphenols in the process for producing alicyclic monoketones and the process for producing alicyclic diketones each of which uses the palladium/alkali metal catalyst (1) is carried out in a solvent, preferably a saturated alcohol of 3 or more carbon atoms, particularly preferably a monohydric saturated aliphatic alcohol of 3 to 12 carbon atoms, in the presence of the palladium/alkali metal catalyst (1).

From the viewpoint of safety, the hydrogenation of the substituted bisphenols is desirably carried out after the system is purged with an inert gas such as a nitrogen gas or an argon gas and then with hydrogen.

In the process for producing alicyclic monoketones and the process for producing alicyclic diketones each of which uses the palladium/alkali metal catalyst (1), the total amount of hydrogen fed to the system in the hydrogenation of the substituted bisphenols is controlled so that the desired product is obtained. When the alicyclic monoketones are intended to be produced, the total amount of hydrogen is only a theoretical amount needed to obtain the alicyclic monoketones. When the alicyclic diketones are intended to be produced, an excess of hydrogen is fed to the reaction system.

In the process for producing alicyclic monoketones using the palladium/alkali metal catalyst (1) according to the invention, the reaction temperature for the hydrogenation is in the range of 100 to 150° C., preferably 120 to 140° C., the hydrogen pressure is in the range of 1 to 10 kg/cm²-G, preferably 2 to 4 kg/cm²-G, and the reaction time is in the range of 2 to 10 hours, preferably 3 to 5 hours.

In the process for producing alicyclic diketones using the palladium/alkali metal catalyst (1) according to the invention, the reaction temperature for the hydrogenation is in the range of 100 to 150° C., preferably 120 to 140° C., the hydrogen pressure is in the range of 1 to 10 kg/cm²-G, preferably 2 to 4 kg/cm²-G, and the reaction time is in the range of 3 to 10 hours, preferably 3 to 8 hours.

Hydrogenation of Substituted Biphenols by Palladium Catalyst (2)

Hydrogenation of the substituted biphenols in the process for producing alicyclic monoketones using the palladium catalyst (2) is carried out in a solvent, preferably a saturated alcohol of 3 or more carbon atoms, particularly preferably a monohydric saturated aliphatic alcohol of 3 to 12 carbon atoms, in the presence of the palladium catalyst (2).

From the viewpoint of safety, the hydrogenation of the substituted biphenols is desirably carried out after the system is purged with an inert gas such as a nitrogen gas or an argon gas and then with hydrogen.

In the process for producing alicyclic monoketones using the palladium catalyst (2) according to the invention, the amount of hydrogen fed to the reaction system is in the range of 1.1 to 1.4 times by mol as much as the theoretical amount (by mol) of hydrogen. The reaction temperature for the hydrogenation is in the range of 100 to 180° C., preferably 110 to 160° C., the hydrogen pressure is in the range of 1 to 10 kg/cm²-G, preferably 2 to 8 kg/cm²-G, and the reaction time is in the range of 2 to 10 hours, preferably 3 to 7 hours.

Alicyclic Monoketones

The alicyclic monoketones obtained by the process for producing alicyclic monoketones using the palladium/alkali metal catalyst (1) according to the invention are represented by the following formula (II). The alicyclic monoketones obtained by the process using the palladium catalyst (2) according to the invention are alicyclic monoketones (hydroxyphenylcyclohexanone derivatives) represented by the formula (II) wherein X is a single bond, namely, those represented by the following formula (II-1).

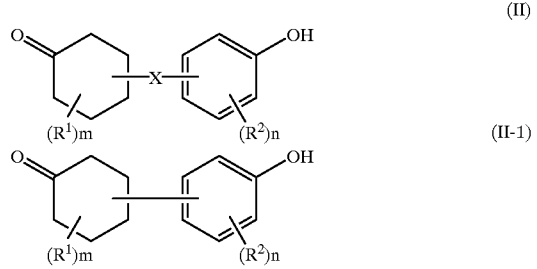

In the formula (II), X, $R^1$, $R^2$, m and n have the same meanings as those of X, $R^1$, $R^2$, m and n in the aforesaid formula (I). In the formula (II-1), $R^1$, $R^2$, m and n have the same meanings as those of $R^1$, $R^2$, m and n in the aforesaid formula (I-1).

Examples of the alicyclic monoketones represented by the formula (II) include:

alicyclic monoketones wherein X is a single bond, such as:

4-oxocyclohexyl-4'-hydroxybenzene, which is a hydrogenated product of bis(4-hydroxyphenyl), 2-oxocyclohexyl-2'-hydroxybenzene, which is a hydrogenated product of bis(2-hydroxyphenyl), and (2-methyl-4-oxocyclohexyl)-2'-methyl-4'-hydroxybenzene, which is a hydrogenated product of bis(2-methyl-4-hydroxyphenyl);

alicyclic monoketones wherein X is a methylene group (—CH$_2$—), such as: (4-oxocyclohexyl)-(4-hydroxyphenyl)methane, which is a hydrogenated product of bis(4-hydroxyphenyl)methane, (2-oxocyclohexyl)-(2-hydroxyphenyl)methane, which is a hydrogenated product of bis(2-hydroxyphenyl)methane, (2-ethyl-4-oxocyclohexyl)-(2-ethyl-4-hydroxyphenyl)methane, which is a hydrogenated product of bis(2-ethyl-4-hydroxyphenyl)methane, and (2-hydroxyphenyl)-(4-oxocyclohexyl)methane and (2-oxocyclohexyl)-(4-hydroxyphenyl)methane, each of which is a hydrogenated product of (2-hydroxyphenyl)-(4-hydroxyphenyl)methane;

alicyclic monoketones wherein X is an isopropylidene group (—C(CH$_3$)$_2$—), such as:

2(4-oxocyclohexyl)-2-(4-hydroxyphenyl)propane, which is a hydrogenated product of bisphenol A, 2-(2-oxocyclohexyl)-2-(2-hydroxyphenyl)propane, which is a hydrogenated product of 2,2-bis(2-hydroxyphenyl)propane, 2-(2-methyl-4-oxocyclohexyl)-2-(2-methyl-4-hydroxyphenyl)propane, which is a hydrogenated product of 2,2-bis(2-methyl-4-hydroxyphenyl)propane, 2-(3-methyl-4-oxocyclohexyl)-2-(3-methyl-4-hydroxyphenyl)propane, which is a hydrogenated product of 2,2-bis(3-methyl-4-hydroxyphenyl)propane, and 2-(2-hydroxyphenyl)-2-(4-oxocyclohexyl)propane and 2-(2-oxocyclohexyl)-2-(4-hydroxyphenyl)propane, each of which is a hydrogenated product of 2-(2-hydroxyphenyl)-2-(4-hydroxyphenyl)propane;

alicyclic monoketones wherein X is an oxygen atom, such as:

(4-oxocyclohexyl)-(4-hydroxyphenyl)ether, which is a hydrogenated product of bis(4-hydroxyphenyl)ether, and (2-oxocyclohexyl)-(2-hydroxyphenyl)ether, which is a hydrogenated product of bis(2-hydroxyphenyl)ether; and alicyclic monoketones wherein X is a sulfonyl group (—SO$_2$—), such as:

(4-oxocyclohexyl)-(4-hydroxyphenyl)sulfone, which is a hydrogenated product of bis(4-hydroxyphenyl)sulfone (i.e., bisphenol S), and (2-methyl-4-oxocyclohexyl)-(2-methyl-4-hydroxyphenyl)sulfone, which is a hydrogenated product of bis(2-methyl-4-hydroxyphenyl)sulfone.

Examples of the alicyclic monoketones represented by the formula (II-1) include the alicyclic monoketones of the formula (II) wherein X is a single bond, which are selected from among the above examples.

Alicyclic Diketones

The alicyclic diketones obtained by the process for producing alicyclic diketones according to the invention are represented by the following formula (III).

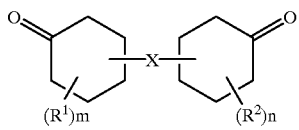

(III)

In the formula (III), X, R$^1$, R$^2$, m and n have the same meanings as those of X, R$^1$, R$^2$, m and n in the aforesaid formula (I).

Examples of the alicyclic diketones represented by the formula (III) include:

alicyclic diketones wherein X is a single bond, such as:

4,4'-bicyclohexanone (i.e., bis(4-oxocyclohexyl)), which is a hydrogenated product of bis(4-hydroxyphenyl), 2,2'-bicyclohexanone (i.e., bis(2-oxocyclohexyl)), which is a hydrogenated product bis(2-hydroxyphenyl), and bis(2-methyl-4-oxocyclohexyl), which is a hydrogenated product of bis(2-methyl-4-hydroxyphenyl);

alicyclic diketones wherein X is a methylene group (—CH$_2$—), such as: bis(4-oxocyclohexyl)methane, which is a hydrogenated product of bis(4-hydroxyphenyl)methane, bis(2-oxocyclohexyl)methane, which is a hydrogenated product of bis(2-hydroxyphenyl)methane, bis(2-ethyl-4-oxocyclohexyl)methane, which is a hydrogenated product of bis(2-ethyl-4-hydroxyphenyl)methane, and (2-oxocyclohexyl)-(4-oxocyclohexyl)methane, which is a hydrogenated product of (2-hydroxyphenyl)-(4-hydroxyphenyl)methane;

alicyclic diketones wherein X is an isopropylidene group (—C(CH$_3$)$_2$—), such as:

2,2-bis(4-oxocyclohexyl)propane, which is a hydrogenated product of 2,2-bis(4-hydroxyphenyl)propane (i.e., bisphenol A), 2,2-bis(2-oxocyclohexyl)propane, which is a hydrogenated product of 2,2-bis(2-hydroxyphenyl)propane, 2,2-bis(2-methyl-4-oxocyclohexyl)propane, which is a hydrogenated product of 2,2-bis(2-methyl-4-hydroxyphenyl)propane, 2,2-bis(3-methyl-4-oxocyclohexyl)propane, which is a hydrogenated product of 2,2-bis(3-methyl-4-hydroxyphenyl)propane, and 2-(2-oxocyclohexyl)-2-(4-oxocyclohexyl)propane, which is a hydrogenated product of 2-(2-hydroxyphenyl)-2-(4-hydroxyphenyl)propane;

alicyclic diketones wherein X is an oxygen atom, such as:

bis(4-oxocyclohexyl)ether, which is a hydrogenated product of bis(4-hydroxyphenyl)ether, and bis(2-oxocyclohexyl)ether, which is a hydrogenated product of bis(2-hydroxyphenyl)ether; and alicyclic diketones wherein X is a sulfonyl group (—SO$_2$—), such as:

bis(4-oxocyclohexyl)sulfone, which is a hydrogenated product of bis(4-hydroxyphenyl)sulfone (i.e., bisphenol S), and bis(2-methyl-4-oxocyclohexyl)sulfone, which is a hydrogenated product of bis(2-methyl-4-hydroxyphenyl)sulfone.

Purification

As described above, hydrogenation of the specific substituted bisphenols is carried out in a solvent in the presence of the palladium/alkali metal catalyst (1) or the palladium catalyst (2) to obtain the desired product, i.e., alicyclic monoketones (hydroxyphenylcyclohexanone derivatives) or alicyclic diketones. The thus produced alicyclic monoketones or alicyclic diketones are purified, if necessary, to obtain final products.

The desired product can be purified by filtering the hydrogenation reaction solution containing the desired product to remove the catalyst and then performing crystallization, filtration and drying.

In the present invention, it is preferable from the viewpoint of purity of the desired product that coarse crystals are obtained from the reaction solvent (e.g., 2-butanol) and recrystallization of the coarse crystals is then performed using another solvent (e.g., methyl ethyl ketone).

Examples of the solvents used in the recrystallization include ketones, such as methyl isobutyl ketone (MIBK), acetone and methyl ethyl ketone (MEK); toluene; and methanol.

EFFECT OF THE INVENTION

According to the process of the invention for producing alicyclic monoketones (hydroxyphenylcyclohexanone derivatives), alicyclic monoketones can be obtained with high selectivity and in high yields through simple steps, because this process includes only one reaction step to hydrogenate substituted bisphenols under relatively mild conditions.

According to the process of the invention for producing alicyclic diketones, alicyclic diketones can be obtained in high yields through simple steps, because this process includes only one reaction step to hydrogenate substituted bisphenols under relatively mild conditions.

EXAMPLE

The present invention is further described with reference to the following examples, but it should be construed that the invention is in no way limited to those examples.

(A) Example of Process for Producing Alicyclic Monoketones (Hydroxyphenylcyclohexanone Derivatives) Using Palladium/alkali Metal Catalyst (1)

Example A-1

Preparation of 2-(4-oxocyclohexyl)-2-(4-hydroxyphenyl)propane

Into 1-liter autoclave, 100 g (0.44 mol) of bisphenol A and 150 g of 2-butanol (sec-butanol) were introduced. To the autoclave were then added 3.1 g (in terms of dry catalyst) of a palladium/alkali metal catalyst (water-containing catalyst) in which 5% by weight of Pd and 1 to 1.5% by weight of Na had been supported on carbon and 0.1 g of sodium carbonate ($Na_2CO_3$) as a co-catalyst.

After the addition was completed, the autoclave (reaction system) was pressurized up to 10 $kg/cm^2$-G with pure nitrogen, followed by pressure releasing. These operations were repeated three times to purge the system with nitrogen.

Subsequently, the system was purged with hydrogen in a manner similar to that of the above-mentioned purging with nitrogen. Thereafter, the temperature in the system was raised. When the temperature reached 140° C., the hydrogen pressure in the system was adjusted to 4 $kg/cm^2$-G, and hydrogen was introduced in a theoretical amount needed for hydrogenation, i.e., 43,206 cc-1 atm.

After the hydrogenation reaction stopped, the reaction solution in the system was cooled to 80° C. Then, the catalyst was removed from the reaction solution by filtration, and the solvent (2-butanol) was recovered by distillation.

Using the bottom solution after removal of the solvent by distillation, identification of the reaction products and composition analyses thereof were carried out by gas chromatography (GC), mass spectra (MS) and $^1$H-NMR (400 MHz). As a result, the yield of the desired product, 2-(4-oxocyclohexyl)-2-(4-hydroxyphenyl)propane, was 80%. As a by-product, 2,2-bis(4-oxocyclohexyl)propane was produced in a yield of 16.9%. The conversion of bisphenol A was 99.1%, and the selectivity of 2-(4-oxocyclohexyl)-2-(4-hydroxyphenyl)propane was 80.3%.

The results are set forth in Table 1.

TABLE 1

|  | Example A-1 |
|---|---|
| Starting material | HPA |
| (g) | 100 |
| Solvent | 2-butanol |
| (g) | 150 |
| Catalyst | 5% Pd-Na/C |
| (g) | 3.1 |
| Co-catalyst | $Na_2CO_3$ |
| (g) | 0.1 |
| Reaction temperature (° C.) | 140 |
| Hydrogen pressure ($kg/cm^2$-G)) | 4 |
| Feed amount of hydrogen (theoretical amount) (cc-1 atm) | 21,516 |
| Reaction time (hr) | 2 |
| Conversion of substituted bisphenol (%) | 99.1 |
| Selectivity of alicyclic monoketone (%) | 80.3 |
| Yield of alicyclic monoketone (%) | 80 |

Note: BPA: Bisphenol A

(B) Examples of Processes for Producing Alicyclic Diketones

Example B-1

Preparation of 2,2-bis(4-oxocyclohexyl)propane

Into 1-liter autoclave, 100 g (0.44 mol) of bisphenol A and 150 g of 2-butanol were introduced. To the autoclave were then added 3.1 g (in terms of dry catalyst) of a palladium/alkali metal catalyst (water-containing catalyst) in which 5% by weight of Pd and 1 to 1.5% by weight of Na had been supported on carbon and 0.1 g of sodium carbonate ($Na_2CO_3$) as a co-catalyst.

After the addition was completed, the autoclave (reaction system) was pressurized up to 10 $kg/cm^2$-G with pure nitrogen, followed by pressure releasing. These operations were repeated three times to purge the system with nitrogen.

Subsequently, the system was purged with hydrogen in a manner similar to that of the above-mentioned purging with nitrogen. Thereafter, the temperature in the system was raised. When the temperature reached 140° C., the hydrogen pressure in the system was adjusted to 4 $kg/cm^2$-G, and hydrogen was introduced until absorption of hydrogen stopped.

After the absorption of hydrogen almost stopped, the reaction solution in the system was cooled to 80° C. To the system was then added 150 g of acetone, and the catalyst was removed from the reaction solution by filtration. Using the resulting solution, composition analyses of the reaction products were carried out by gas chromatography (GC) and mass spectra (MS). As a result, the selectivity of the desired product, 2,2-bis(4-oxocyclohexyl)propane, was 65.8%.

Then, the reaction solution after removal of the catalyst by filtration was cooled to 30° C. The crystals precipitated were filtered and washed with a mixed solvent of 30 g of acetone and 30 g of 2-butanol to obtain coarse crystals.

To the coarse crystals thus obtained was added 153 g of 2-butanol to dissolve the coarse crystals in 2-butanol, followed by recrystallization. The crystals precipitated were filtered and dried to obtain purified crystals. The purified crystals thus obtained were identified by $^1$H-NMR (400 MHz). As a result, the purified crystals were found to be 2,2-bis(4-oxocyclohexyl)propane. The purity of the purified crystals was 99%.

The results are set forth in Table 2.

Example B-2

Preparation of 2,2-bis(4-oxocyclohexyl)propane 2,2-Bis(4-oxocyclohexyl)propane was obtained in the same manner as in Example B-1, except that the hydrogenation reaction temperature was changed to 150° C. and the hydrogen pressure was changed to 5 kg/cm$^2$-G. The purity of the purified 2,2-bis(4-oxocyclohexyl)propane was 96.69%.

Further, identification of the reaction products and composition analyses thereof were carried out by gas chromatography (GC), mass spectra (MS) and $^1$H-NMR (400 MHz) in the same manner as in Example B-1. As a result, the yield of the desired product, 2,2-bis(4-oxocyclohexyl)propane, was 58.9%. The conversion of bisphenol A was 100%, and the selectivity of 2,2-bis(4-oxocyclohexyl)propane was 58.9%.

The results are set forth in Table 2.

Example B-3

Preparation of 2,2-bis(4-oxocyclohexyl)propane 2,2-Bis(4-oxocyclohexyl)propane was obtained in the same manner as in Example B-1, except that 2-octanol was used instead of 2-butanol, the hydrogenation reaction temperature was changed to 150° C. and the hydrogen pressure was changed to 2.0 kg/cm$^2$-G.

Further, identification of the reaction products and composition analyses thereof were carried out by gas chromatography (GC), mass spectra (MS) and $^1$H-NMR (400 MHz) in the same manner as in Example B-1. As a result, the yield of the desired product, 2,2-bis(4-oxocyclohexyl)propane, was 58.2%. The conversion of bisphenol A was 100%, and the selectivity of 2,2-bis(4-oxocyclohexyl)propane was 58.2%.

The results are set forth in Table 2.

Example B-4

Preparation of 2,2-bis(4-oxocyclohexyl)propane 2,2-Bis(4-oxocyclohexyl)propane was obtained in the same manner as in Example B-1, except that the amount of the palladium/alkali metal catalyst and the amount of the co-catalyst were changed to 3.0 g and 0 g, respectively, the hydrogenation reaction temperature was changed to 150° C., the hydrogen pressure was changed to 5 kg/cm$^2$-G and the reaction time was changed to 2 hours. The purity of the purified 2,2-bis(4-oxocyclohexyl)propane was 99%.

Further, identification of the reaction products and composition analyses thereof were carried out by gas chromatography (GC), mass spectra (MS) and $^1$H-NMR (400 MHz) in the same manner as in Example B-1. As a result, the yield of the desired product, 2,2-bis(4-oxocyclohexyl)propane, was 55.0%. The conversion of bisphenol A was 100%, and the selectivity of 2,2-bis(4-oxocyclohexyl)propane was 55.0%.

The results are set forth in Table 2.

Comparative Example B-1

Preparation of 2,2-bis(4-oxocyclohexyl)propane 2,2-Bis(4-oxocyclohexyl)propane was obtained in the same manner as in Example B-1, except that 3.1 g (in terms of dry catalyst) of a palladium catalyst (water-containing catalyst) in which 5% by weight of Pd had been supported on carbon was used instead of the palladium/alkali metal catalyst, the hydrogenation reaction temperature was changed to 150° C. and the hydrogen pressure was changed to 5 kg/cm$^2$-G.

Further, identification of the reaction products and composition analyses thereof were carried out by gas chromatography (GC), mass spectra (MS) and $^1$H-NMR (400 MHz) in the same manner as in Example B-1. As a result, the yield of the desired product, 2,2-bis(4-oxocyclohexyl)propane, was 39.3%. The conversion of bisphenol A was 100%, and the selectivity of 2,2-bis(4-oxocyclohexyl)propane was 39.3%

The results are set forth in Table 3.

Comparative Example B-2

Preparation of 2,2-bis(4-oxocyclohexyl)propane

The procedure of Example B-1 was repeated, except that methanol was used instead of 2-butanol, the hydrogenation reaction temperature was changed to 150° C. and the hydrogen pressure was changed to 8.6 kg/cm$^2$-G. However, any reaction product was not detected.

Comparative Example B-3

Preparation of 2,2-bis(4-oxocyclohexyl)propane 2,2-Bis(4-oxocyclohexyl)propane was obtained in the same manner as in Example B-1, except that cyclohexanol was used instead of 2-butanol, the hydrogenation reaction temperature was changed to 150° C. and the hydrogen pressure was changed to 2.0 kg/cm$^2$-G.

Further, identification of the reaction products and composition analyses thereof were carried out by gas chromatography (GC), mass spectra (MS) and $^1$H-NMR (400 MHz) in the same manner as in Example B-1. As a result, the yield of the desired product, 2,2-bis(4-oxocyclohexyl)propane, was 21.1%. The conversion of bisphenol A was 100%, and the selectivity of 2,2-bis(4-oxocyclohexyl)propane was 21.1%.

The results are set forth in Table 3.

Comparative Example B-4

Preparation of 2,2-bis(4-oxocyclohexyl)propane 2,2-Bis(4-oxocyclohexyl)propane was obtained in the same manner as in Example B-1, except that 3.1 g (in terms of dry catalyst) of a palladium catalyst (water-containing catalyst) in which 5% by weight of Pd had been supported on carbon was used instead of the palladium/alkali metal catalyst, polyalkylbenzene (trade name: Solvesso 150, available from Exxon Chemical Co.) was used instead of 2-butanol, the hydrogenation reaction temperature was changed to 170° C. and the hydrogen pressure was changed to 5 kg/cm$^2$-G.

Further, identification of the reaction products and composition analyses thereof were carried out by gas chromatography (GC), mass spectra (MS) and $^1$H-NMR (400 MHz) in the same manner as in Example B-1. As a result, the yield of the desired product, 2,2-bis(4-oxocyclohexyl)propane, was 45.7%. The conversion of bisphenol A was 100%, and the selectivity of 2,2-bis(4-oxocyclohexyl)propane was 45.7%.

The results are set forth in Table 3.

TABLE 2

|  | Example B-1 | Example B-2 | Example B-3 | Example B-4 |
|---|---|---|---|---|
| Starting material (g) | BPA 100 | BPA 100 | BPA 100 | BPA 100 |
| Solvent (g) | 2-buthanol 150 | 2-buthanol 150 | 2-octanol 150 | 2-buthanol 150 |
| Catalyst (g) | 5% Pd-Na/C 3.1 | 5% Pd-Na/C 3.1 | 5% Pd-Na/C 3.1 | 5% Pd-Na/C 3.0 |
| Co-catalyst (g) | $Na_2CO_3$ 0.1 | $Na_2CO_3$ 0.1 | $Na_2CO_3$ 0.1 | — |
| Reaction temperature (° C.) | 140 | 150 | 150 | 150 |
| Hydrogen pressure ($kg/cm^2$-G) | 4 | 5 | 2.0 | 5 |
| Reaction time (hr) | 4 | 4 | 4 | 2 |
| Conversion of substituted bisphenol (%) | 100 | 100 | 100 | 100 |
| Selectivity of alicyclic diketone (%) | 65.8 | 58.9 | 58.2 | 55.0 |
| Yield of alicyclic Diketone (%) | 65.8 | 58.9 | 58.2 | 55.0 |

Note: BPA: Bisphenol A

TABLE 3

|  | Comp. Ex. B-1 | Comp. Ex. B-2 | Comp. Ex. B-3 | Comp. Ex. B-4 |
|---|---|---|---|---|
| Starting material (g) | BPA 100 | BPA 100 | BPA 100 | BPA 100 |
| Solvent (g) | 2-buthanol 150 | Methanol 150 | Cyclohexanol 150 | Solvesso 150 |
| Catalyst (g) | 5% Pd/C 3.1 | 5% Pd-Na/C 3.1 | 5% Pd-Na/C 3.1 | 5% Pd/C 3.1 |
| Co-catalyst (g) | $Na_2CO_3$ 0.1 | $Na_2CO_3$ 0.1 | $Na_2CO_3$ 0.1 | $Na_2CO_3$ 0.1 |
| Reaction temperature (° C.) | 150 | 150 | 150 | 170 |
| Hydrogen pressure ($kg/cm^2$-G) | 5 | 8.6 | 2.0 | 5 |
| Reaction time (hr) | 5 | Not reacted | 4 | 3 |
| Conversion of substituted bisphenol (%) | 100 | 0 | 100 | 100 |
| Selectivity of alicyclic diketone (%) | 39.3 | 0 | 21.1 | 45.7 |
| Yield of alicyclic Diketone (%) | 39.3 | 0 | 21.1 | 45.7 |

Note 1: BPA: Bisphenol A
Note 2: Solvesso: Solvesso 150 (trade name), polyalkylbenzene available from Exxon Chemical Co.

Example B-5

Preparation of 4,4'-bicyclohexanone

Into 1-liter autoclave, 100 g (0.54 mol) of biphenol and 150 g of 2-butanol were introduced. To the autoclave was then added 1 g (in terms of dry catalyst) of a palladium/alkali metal catalyst (water-containing catalyst) in which 5% by weight of Pd and 1 to 1.5% by weight of Na had been supported on carbon.

After the addition was completed, the autoclave (reaction system) was pressurized up to 10 $kg/cm^2$-G with pure nitrogen, followed by pressure releasing. These operations were repeated three times to purge the system with nitrogen.

Subsequently, the system was purged with hydrogen in a manner similar to that of the above-mentioned purging with nitrogen. Thereafter, the temperature in the system was raised. When the temperature reached 140° C., the hydrogen pressure in the system was adjusted to 4 $kg/cm^2$-G, and hydrogen was introduced until absorption of hydrogen stopped.

After the absorption of hydrogen almost stopped, the reaction solution in the system was cooled to 80° C., and the catalyst was removed from the reaction solution by filtration. Using the resulting solution, composition analyses of the reaction products were carried out by gas chromatography (GC) and mass spectra (MS). As a result, the yield of the desired product, 4,4'-bicyclohexanone, was 72%.

Then, the reaction solution after removal of the catalyst by filtration was cooled to 30° C. The crystals precipitated were filtered and dried to obtain purified crystals. The purified crystals thus obtained were identified by $^1$H-NMR (400 MHz). As a result, the purified crystals were found to be 4,4'-bicyclohexanone. The purity of the purified crystals was 99%.

The results are set forth in Table 4.

Example B-6

Preparation of 4,4'-bicyclohexanone 4,4'-Bicyclohexanone was obtained in the same manner as in Example B-5, except that the amount of the palladium/alkali metal catalyst was changed to 3 g and 0.1 g of sodium carbonate was used as a co-catalyst.

Further, identification of the reaction products and composition analyses thereof were carried out by gas chromatography (GC), mass spectra (MS) and $^1$H-NMR (400 MHz) in the same manner as in Example B-5. As a result, the yield of the desired product, 4,4'-bicyclohexanone, was 66.1%. The conversion of biphenol was 99.9%, and the selectivity of 4,4'-bicyclohexanone was 66.2%.

The results are set forth in Table 4.

Example B-7

Preparation of 4,4'-bicyclohexanone 4,4'-Bicyclohexanone was obtained in the same manner as in Example B-5, except that the amount of the palladium/alkali metal catalyst was changed to 1.5 g and the reaction time was changed to 4 hours.

Further, identification of the reaction products and composition analyses thereof were carried out by gas chromatography (GC), mass spectra (MS) and $^1$H-NMR (400 MHz) in the same manner as in Example B-5. As a result, the yield of the desired product, 4,4-bicyclohexanone, was 59%. The conversion of biphenol was 99.8%, and the selectivity of 4,4'-bicyclohexanone was 77%.

The results are set forth in Table 4.

TABLE 4

|  | Example B-5 | Example B-6 | Example B-7 |
|---|---|---|---|
| Starting material (g) | BP 100 | BP 100 | BP 100 |
| Solvent (g) | 2-buthanol 150 | 2-buthanol 150 | 2-buthanol 150 |

TABLE 4-continued

|  | Example B-5 | Example B-6 | Example B-7 |
|---|---|---|---|
| Catalyst | 5% Pd-Na/C | 5% Pd-Na/C | 5% Pd-Na/C |
| (g) | 1 | 3 | 1.5 |
|  | — | Na$_2$CO$_3$ | — |
| Co-catalyst |  | 0.1 |  |
| (g) |  |  |  |
| Reaction temperature (° C.) | 140 | 140 | 140 |
| Hydrogen pressure (kg/cm$^2$-G) | 4 | 4 | 4 |
| Reaction time (hr) | 7 | 3 | 4 |
| Conversion of substituted bisphenol (%) | 96 | 99.9 | 99.8 |
| Selectivity of alicyclic diketone (%) | 72 | 66.2 | 77 |
| Yield of alicyclic Diketone (%) | 69 | 66.1 | 59 |

Note: BP: Biphenol

(C) Examples of Processes for Producing Alicyclic Monoketones (Hydroxyphenylcyclohexanone Derivatives) Using Palladium Catalyst (2)

Example C-1

Preparation 4-(4'-hydroxyphenyl)cyclohexanone

Into 1-liter autoclave, 100 g of bis(4-hydroxyphenyl) and 150 g of 2-butanol (sec-butanol) were introduced. To the autoclave was then added 0.5 g (in terms of dry catalyst) of a palladium catalyst (water-containing catalyst) in which 20% by weight of Pd had been supported on carbon.

After the addition was completed, the temperature in the autoclave (reaction system) was raised up to 95° C., and then the pressure was released to adjust the pressure indicator to 0 kg/cm$^2$-G. After the autoclave was closed, the temperature was raised up to 125° C., and a hydrogen gas was occasionally fed through a hydrogen feed opening, whereby the internal pressure was adjusted so that the hydrogen gas pressure in the system was kept constant at 4 kg/cm$^2$-G independent of hydrogen absorption due to the hydrogenation reaction. Under such conditions, the hydrogenation reaction was performed for 6 hours. The conversion of the starting material after completion of the hydrogenation reaction was 95.8%, and the selectivity of 4-(4'-hydroxyphenyl)cyclohexanone was 68.6%.

After the hydrogenation reaction was completed, the temperature in the system was lowered to 95° C. and the system was purged with a nitrogen gas. To the system was then added 250 g of 2-butanol, and the catalyst was filtered out at 70° C. After 200 g of 2-butanol was distilled off from the filtrate at atmospheric pressure to concentrate the filtrate, seed crystals of 4-(4'-hydroxyphenyl)cyclohexanone were added at 82° C., and the temperature was lowered to 30° C. over a period of 6 hours to perform crystallization.

The crystals precipitated were filtered off at 30° C. and dried to obtain 69.7 g of coarse crystals of 4-(4'-hydroxyphenyl)cyclohexanone (purity: 89.8%). To the coarse crystals was added 209 g of methyl ethyl ketone, and they were heated to dissolve the coarse crystals in methyl ethyl ketone. Then, seed crystals of 4-(4'-hydroxyphenyl) cyclohexanone were added at 80° C., followed by cooling to 30° C. over a period of 5 hours to perform recrystallization. The crystals precipitated were filtered off at 30° C. to obtain 45.4 g of purified crystals of 4-(4'-hydroxyphenyl) cyclohexanone. The purity of 4-(4'-hydroxyphenyl) cyclohexanone was 99.0%, and the isolated yield thereof was 44.0%.

The purified crystals thus obtained were identified by $^1$H-NMR (400 MHz), mass spectrum and infrared absorption spectrum. The conversion of bis(4-hydroxyphenyl) used as the starting material, the selectivity of the resulting 4-(4'-hydroxyphenyl)cyclohexanone and the purity thereof were analyzed by gas chromatography.

The results are set forth in Table 5.

Example C-2

Preparation 4-(4'-hydroxyphenyl)cyclohexanone 4-(4'-Hydroxyphenyl)cyclohexanone was obtained in the same manner as in Example C-1, except that the palladium catalyst was replaced with 1.0 g (in terms of dry catalyst) of a palladium catalyst (water-containing catalyst) in which 10% by weight of Pd had been supported on carbon, the hydrogenation reaction temperature was changed to 140° C. and the reaction time was changed to 5.5 hours. The conversion of 4,4'-biphenyldiol as the starting material was 97.7%, and the selectivity of 4-(4'-hydroxyphenyl) cyclohexanone was 62.3%. The coarse crystals of 4-(4'-hydroxyphenyl)cyclohexanone were obtained in amounts of 59.9 g, and the purity of the coarse crystals was 88.5%. The purified crystals were obtained in amounts of 42.6 g, the purity of the purified crystals was 98.0%, and the isolated yield thereof was 40.9%.

The results are set forth in Table 5.

Comparative Example C-1

Preparation 4-(4'-hydroxyphenyl)cyclohexanone 4-(4'-Hydroxyphenyl)cyclohexanone was obtained in the same manner as in Example C-1, except that the palladium catalyst was replaced with 2.0 g (in terms of dry catalyst) of a palladium catalyst (water-containing catalyst) in which 5% by weight of Pd had been supported on carbon, the hydrogenation reaction temperature was changed to 140° C. and the reaction time was changed to 4.1 hours. The conversion of 4,4'-biphenyldiol as the starting material was 97.8%, and the selectivity of 4-(4'-hydroxyphenyl)cyclohexanone was 56.8%. The coarse crystals of 4-(4'-hydroxyphenyl) cyclohexanone were obtained in amounts of 56.8 g, and the purity of the coarse crystals was 76.2%. The purified crystals were obtained in amounts of 37.6 g, the purity of the purified crystals was 92.1%, and the isolated yield thereof was 33.9%.

The results are set forth in Table 6.

Comparative Example C-2

Preparation 4-(4'-hydroxyphenyl)cyclohexanone 4-(4'-Hydroxyphenyl)cyclohexanone was obtained in the same manner as in Example C-1, except that the palladium catalyst was replaced with 2.0 g (in terms of dry catalyst) of a palladium catalyst (water-containing catalyst) in which 5% by weight of Pd had been supported on alumina, the hydrogenation reaction temperature was changed to 140° C. and the reaction time was changed to 6.9 hours. The conversion of 4,4'-biphenyldiol as the starting material was 99.5%, and the selectivity of 4-(4'-hydroxyphenyl)cyclohexanone was 55.7%. The coarse crystals of 4-(4'-hydroxyphenyl) cyclohexanone were obtained in amounts of 54.9 g, and the purity of the coarse crystals was 75.7%. The purified crystals were obtained in amounts of 37.6 g, the purity of the purified crystals was 89.3%, and the isolated yield thereof was 32.9%.

The results are set forth in Table 6.

Comparative Example C-3

Preparation 4-(4'-hydroxyphenyl)cyclohexanone 4-(4'-Hydroxyphenyl)cyclohexanone was obtained in the same manner as in Example C-1, except that 1.0 g (in terms of dry catalyst) of a palladium/alkali metal catalyst (water-containing catalyst) in which 5% by weight of Pd and about 1.5% by weight of Na had been supported on carbon was used instead of the palladium catalyst, the hydrogenation reaction temperature was changed to 140° C., and the reaction time was changed to 5.8 hours. The conversion of 4,4'-biphenyldiol as the starting material was 95.2%, and the selectivity of 4-(4'-hydroxyphenyl)cyclohexanone was 47.3%.

The results are set forth in Table 6.

TABLE 5

|  | Example C-2 | Example C-2 |
| --- | --- | --- |
| Starting material | BHP | BHP |
| (g) | 100 | 100 |
| Solvent | 2-butanol | 2-butanol |
| (g) | 150 | 150 |
| Catalyst | 20% Pd/C | 10% Pd/C |
| (g) | 0.5 | 1.0 |
| Co-catalyst | None | None |
| (g) |  |  |
| Reaction temperature (C) | 125 | 140 |
| Hydrogen pressure (kg/cm²-G) | 4 | 4 |
| Reaction time (hr) | 6 | 5.5 |
| Conversion of substituted biphenols (%) | 95.8 | 97.7 |
| Selectivity of desired product (%) | 68.6 | 62.3 |
| Coarse crystals |  |  |
| Purity (%) | 89.8 | 88.5 |
| Yield (%) | 61.3 | 52.0 |
| Purified crystals |  |  |
| Purity (%) | 99.0 | 98.0 |
| Yield (%) | 44.0 | 40.9 |

Note 1: BHP: Bis(4-hydroxyphenyl)
Note 2: Catalyst: Amount in terms of dry catalyst of water-containing catalyst
Note 3: Desired product: 4-(4'-hydroxyphenyl)cyclohexanone

TABLE 6

|  | Compar. Ex. C-1 | Compar. Ex. C-2 | Compar. Ex. C-2 |
| --- | --- | --- | --- |
| Starting material | BHP | BHP | BHP |
| (g) | 100 | 100 | 100 |
| Solvent | 2-buthanol | 2-buthanol | 2-buthanol |
| (g) | 150 | 150 | 150 |
| Catalyst | 5% Pd/C | 5% Pd/Al₂O₃ | 5% Pd-Na/C |
| (g) | 2.0 | 2.0 | 1.0 |
| Co-catalyst (g) | None | None | None |
| Reaction temperature (° C.) | 140 | 140 | 140 |
| Hydrogen pressure (kg/cm²-G) | 4 | 4 | 4 |
| Reaction time (hr) | 4.1 | 6.9 | 5.8 |
| Conversion of substituted biphenol (%) | 97.8 | 99.5 | 95.2 |
| Selectivity of desired product (%) | 56.5 | 55.7 | 47.3 |
| Coarse crystals |  |  |  |
| Purity (%) | 76.2 | 75.7 | — |
| Yield (%) | 42.4 | 40.7 | — |
| Purified crystals |  |  |  |
| Purity (%) | 92.1 | 89.3 | — |
| Yield (%) | 33.9 | 32.9 | — |

Note 1: BHP: Bis(4-hydroxyphenyl)
Note 2: Catalyst: Amount in terms of dry catalyst of water-containing catalyst
Note 3: Desired product: 4-(4'-hydroxyphenyl)-cyclohexanone

What is claimed is:

1. A process for producing alicyclic monoketones, comprising hydrogenating substituted bisphenols represented by the following formula (I) in a solvent in the presence of a palladium/alkali metal catalyst in which palladium and an alkali metal are both supported on a carrier, to obtain alicyclic monoketones represented by the following formula (II);

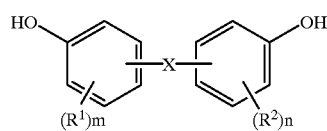

(I)

wherein
X is a —CH₂—, —C(CH₃)₂—, —O— or —SO₂—;
R¹ and R² are each independently a hydrogen atom or an alkyl group of 1 to 6 carbon atoms; and m and n are each an integer of 0 to 2 and are the same or different;

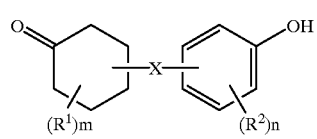

(II)

wherein X, R¹, R², m and n in formula (II) have the same meanings as those of X, R¹, R², m and n in the formula (I).

2. The process fox producing alicyclic monoketones as claimed in claim 1, wherein the substituted bisphenols are bis(4-hydroxyphenyl)methane, bis(2-hydroxyphenyl)methane, bis(2-ethyl-4-hydroxyphenyl)methane, (2-hydroxyphenyl)-(4-hydroxyphenyl)methane, bisphenol A, 2,2-bis(2-hydroxyphenyl)propane, 2,2-bis(2-methyl-4-hydroxyphenyl)propane, 2,2-bis(3-methyl-4-hydroxyphenyl)propane, 2-(2-hydroxyphenyl)-2-(4-hydroxyphenyl)propane, bis(4-hydroxyphenyl)ether, bis(2-hydroxyphenyl)ether, bis(4-hydroxyphenyl)sulfone and bis(2-m-ethyl-4-hydroxyphenyl)sulfone.

3. The process for producing alicyclic monoketones as claimed in claim 2, wherein the palladium/alkali metal catalyst is a catalyst in which 1 to 10% by weight of palladium and 0.5 to 5% by weight of an alkali metal are both supported on a carrier.

4. The process for producing alicyclic monoketones as claimed in claim 3, wherein the solvent is a monohydric saturated aliphatic alcohol of 3 to 12 carbon atoms.

5. The process for producing alicyclic monoketones as claimed in claim 2, wherein the solvent is a monohydric saturated aliphatic alcohol of 3 to 12 carbon atoms.

6. The process for producing alicyclic monoketones as claimed in claim 1, wherein the palladium/alkali metal catalyst is a catalyst in which 1 to 10% by weight of palladium and 0.5 to 5% by weight of an alkali metal are both supported on a carrier.

7. The process for producing alicyclic monoketones as claimed in claim 6, wherein the solvent is a monohydric saturated aliphatic alcohol of 3 to 12 carbon atoms.

8. The process for producing alicyclic monoketones as claimed in claim 1, wherein the solvent is a monohydric saturated aliphatic alcohol of 3 to 12 carbon atoms.

9. A process for producing alicyclic diketones, comprising hydrogenating substituted bisphenols represented by the following formula (I) in a solvent in the presence of a palladium/alkali metal catalyst in which palladium and an alkali metal are both supported on a carrier, wherein the solvent is a monohydric saturated aliphatic alcohol of 3 to 12 carbon atoms, to obtain alicyclic diketones represented by the following formula (III);

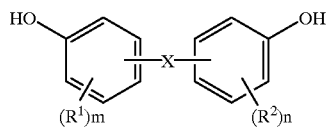

(I)

wherein X is a single bond, —CH$_2$—, —C(CH$_3$)$_2$—, —O— or —SO$_2$—; and R' are each independently a hydrogen atom ox an alkyl group of 1 to 6 carbon atoms: and m and n are each an integer of 0 to 2 and are the same or different;

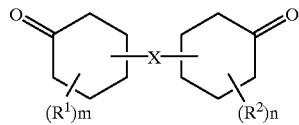

(III)

wherein X, R$^1$, R$^2$, m and n in formula (III) have the same meaning as those of X, R$^1$, R$^2$, m and n in the formula (I).

10. The process for producing alicyclic diketones as claimed in claim 9, wherein the substituted bisphenols are bis(4-hydroxyphenyl), bis(2-hydroxyphenyl), bis(2-methyl-4-hydroxyphenyl), bis(4-hydroxyphenyl)methane, bis(2-hydroxyphenyl)methane, bis(2-ethyl-4-hydroxyphenyl)methane, (2-hydroxyphenyl)-(4-hydroxyphenyl)methane, bisphenol A, 2,2-bis(2-hydroxyphenyl)propane, 2,2-bis(2-methyl-4-hydroxyphenyl)propane, 2,2-bis(3-methyl-4-hydroxyphenyl)propane, 2-(2-hydroxyphenyl)-2-(4-hydroxyphenyl)propane, bis(4-hydroxyphenyl)ether, bis(2-hydroxyphenyl)ether, bis(4-hydroxyphenyl)sulfone and bis(2-methyl-4-hydroxyphenyl)sulfone.

11. The process for producing alicyclic diketones as claimed in claim 10, wherein the palladium/alkali metal catalyst is a catalyst in which 1 to 10% by weight of palladium and 0.5 to 5% by weight of an alkali metal are both supported on a carrier.

12. The process for producing alicyclic diketones as claimed in claim 11, wherein the solvent is a monohydric saturated aliphatic alcohol of 3 to 12 carbon atoms.

13. The process for producing alicyclic diketones as claimed in claim 10, wherein the solvent is a monohydric saturated aliphatic alcohol of 3 to 12 carbon atoms.

14. The process for producing alicyclic diketones as claimed in claim 9, wherein the palladium/alkali metal catalyst is a catalyst in which 1 to 10% by weight of palladium and 0.5 to 5% by weight of an alkali metal are both supported on a carrier.

15. The process for producing alicyclic diketones as claimed in claim 14, wherein the solvent is a monohydric saturated aliphatic alcohol of 3 to 12 carbon atoms.

16. The process for producing alicyclic monoketones as claimed in claim 9, wherein the solvent is a monohydric non-cyclic saturated aliphatic alcohol of 3 to 12 carbon atoms.

17. A process for producing alicyclic monoketones, comprising hydrogenating substituted biphenols represented by the following formula (I-1) in an organic solvent in the presence of a palladium catalyst in which 10 to 30% by weight of palladium is supported on a carrier, to obtain alicyclic monoketones represented by the following formula (II-1);

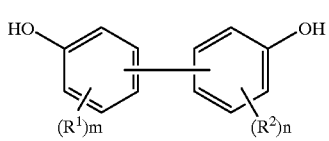

(I-1)

wherein R$^1$ and R$^2$ are each independently a hydrogen atom or an alkyl group of 1 to 6 carbon atoms; and m and n are each an integer of 0 to 2 and are the same or different;

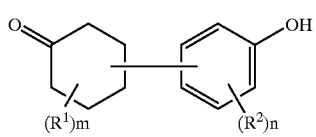

(II-1)

wherein R$^1$, R$^2$, m and n in formula (II-1) have the same meaning as those of R$^1$, R$^2$, m and n in the formula (I-1).

18. The process for producing alicyclic monoketones as claimed in claim 17, wherein the organic solvent is a monohydric saturated aliphatic alcohol of 3 to 12 carbon atoms.

19. The process for producing alicyclic monoketones as claimed in claim 1, wherein the solvent is a monohydric non-cyclic saturated aliphatic alcohol of 3 to 12 carbon atoms.

20. The process for producing alicyclic monoketones as claimed in claim 17, wherein the organic solvent is a monohydric non-cyclic saturated aliphatic alcohol of 3 to 12 carbon atoms.

21. The process for producing alicyclic monoketones as claimed in claim 17, wherein any co-catalyst is not used in hydrogenating substituted biphenols.

* * * * *